(12) United States Patent
Shao et al.

(10) Patent No.: US 10,925,582 B2
(45) Date of Patent: Feb. 23, 2021

(54) METHOD AND DEVICE FOR SELECTING DETECTION AREA, AND ELASTICITY DETECTION SYSTEM

(71) Applicant: WUXI HISKY MEDIAL TECHNOLOGIES CO., LTD., Wuxi (CN)

(72) Inventors: Jinhua Shao, Wuxi (CN); Jin Sun, Wuxi (CN); Houli Duan, Wuxi (CN)

(73) Assignee: WUXI HISKY MEDICAL TECHNOLOGIES CO., LTD., Wuxi (CN)

(*) Notice: Subject to any disclaimer, the term of this patent is extended or adjusted under 35 U.S.C. 154(b) by 873 days.

(21) Appl. No.: 15/478,021

(22) Filed: Apr. 3, 2017

(65) Prior Publication Data

US 2017/0202540 A1 Jul. 20, 2017

Related U.S. Application Data

(63) Continuation of application No. PCT/CN2015/081817, filed on Jun. 18, 2015.

(30) Foreign Application Priority Data

Oct. 21, 2014 (CN) .......................... 201410561699.9

(51) Int. Cl.
*A61B 8/00* (2006.01)
*A61B 8/08* (2006.01)
(Continued)

(52) U.S. Cl.
CPC ............ *A61B 8/485* (2013.01); *A61B 5/0037* (2013.01); *A61B 5/055* (2013.01); *A61B 5/0555* (2013.01);
(Continued)

(58) Field of Classification Search
CPC ................................ A61B 8/469; A61B 8/485
See application file for complete search history.

(56) References Cited

U.S. PATENT DOCUMENTS

| 2004/0101176 A1 | 5/2004 | Mendonca et al. ........... 382/128 |
| 2008/0221450 A1* | 9/2008 | Kim ..................... A61B 8/0883 |
| | | 600/443 |

(Continued)

FOREIGN PATENT DOCUMENTS

| CN | 1502310 A | 6/2004 |
| CN | 102871686 A | 1/2013 |

(Continued)

OTHER PUBLICATIONS

The Japanese Examination Report of corresponding Japan patent application No. 2017-512997, dated Jan. 16, 2019.
(Continued)

*Primary Examiner* — Rajeev P Siripurapu
(74) *Attorney, Agent, or Firm* — J.C. Patents (57) ABSTRACT

A method and a device for selecting a detection area and an elasticity detection system. The method comprises: dividing organ tissue information to be recognized into a plurality of detection sub-areas, and calculating a feature value of the organ tissue information in the detection sub-area; determining an organ tissue boundary area according to the organ tissue information to be recognized; and determining an organ tissue boundary area according to the organ tissue boundary area and a preset feature value condition. The method can determine the organ tissue boundary according to the organ tissue information, and automatically adjust the detection area according to the organ tissue boundary.

14 Claims, 8 Drawing Sheets

(51) Int. Cl.
*A61B 5/055* (2006.01)
*A61B 6/03* (2006.01)
*A61B 5/00* (2006.01)
*A61B 6/00* (2006.01)

(52) U.S. Cl.
CPC .............. *A61B 5/4244* (2013.01); *A61B 6/03* (2013.01); *A61B 6/032* (2013.01); *A61B 6/5217* (2013.01); *A61B 8/469* (2013.01); *A61B 8/483* (2013.01); *A61B 8/5223* (2013.01); *A61B 5/004* (2013.01); *A61B 5/0035* (2013.01); *A61B 5/4222* (2013.01); *A61B 8/08* (2013.01); *A61B 8/486* (2013.01); *A61B 8/488* (2013.01); *A61B 2576/02* (2013.01)

(56) References Cited

U.S. PATENT DOCUMENTS

| | | | |
|---|---|---|---|
| 2009/0198130 A1 | 8/2009 | Osaka | 600/438 |
| 2010/0081931 A1 | 4/2010 | Destrempes et al. | 600/437 |
| 2010/0160778 A1 | 6/2010 | Eskandari et al. | 600/438 |
| 2011/0194748 A1 | 8/2011 | Tonomura et al. | 382/131 |
| 2013/0085387 A1 | 4/2013 | Chen et al. | 600/439 |
| 2014/0249417 A1 | 9/2014 | Ookouchi et al. | 600/443 |
| 2015/0078640 A1* | 3/2015 | Guo | G06T 7/11 382/131 |

FOREIGN PATENT DOCUMENTS

| | | |
|---|---|---|
| CN | 102956035 A | 3/2013 |
| CN | 203280412 U | 11/2013 |
| CN | 103720489 A | 4/2014 |
| CN | 103874464 A | 6/2014 |
| CN | 104334086 A | 2/2015 |
| CN | 104398272 A | 3/2015 |
| CN | 204379311 U | 6/2015 |
| EP | 2 784 749 A1 | 10/2014 |
| JP | 2003-334194 A | 11/2003 |
| JP | 2007-275456 A | 10/2007 |
| JP | 2008-154626 A | 7/2008 |
| RU | 2 526 752 C1 | 8/2014 |
| WO | WO 2007/135884 A1 | 11/2007 |
| WO | WO 2007/142255 A1 | 12/2007 |
| WO | WO 2010/044385 A1 | 4/2010 |
| WO | WO 2013/155300 A1 | 10/2013 |
| WO | WO 2013/183432 A1 | 12/2013 |

OTHER PUBLICATIONS

The Australian official Examination Report No. 1 of corresponding Australian standard patent application No. 2015335554, dated Jan. 24, 2018.
The Korean official Examination Report of corresponding Republic of Korea patent application No. 10-2017-7006749, dated Feb. 20, 2018.
International Search Report of corresponding International PCT Application No. PCT/CN2015/081817, dated Sep. 22, 2015.
Chinese First Examination Report of corresponding Chinese patent Application No. 201410561699.9, dated Feb. 1, 2016.
Larrue, A. et al., "Nakagami Imaging with Small Windows" 2011 8th IEEE International Symposium on Biomedical Imaging: From Nano to Macro; (Mar. 30, 2011); pp. 887-890.
Larrue, Aymeric et al. "Modeling of Erors in Nakagami Imaging: Illustration on Breast Mass Characterization" Ultrasound in Medicine & Biology; vol. 40, No. 5; (May 1, 2014); pp. 917-930.
Massoptier, Laurent et al., "A new fully automatic and roubst algorithm for fast segmentation of liver tissue and tumors from CT scans" European Radiology; vol. 18, No. 8; (Mar. 28, 2008); pp. 1658-1665.
Saxena, Sanjay et al., "An Intelligent System for Segmenting an Abdominal Image in Multi core Architecture" 2013 10th International Conference and Expo on Emerging Technologies for a Smarter World (CEWIT); (Oct. 21, 2013); pp. 1-6.
Tsui, Po-Hsiang et al., "Ultrasonic Nakagami Imaging: A Strategy to Visualize the Scatterer Properties of Benign and Malignant Breast Tumors" Ultrasound in Medicine & Biology; vol. 36, No. 2; (Feb. 1, 2010); pp. 209-217.
Yap, M.H. et al., "Fully automatic lesion boundary detection in ultrasound breast images" Medical Imaging 2007: Image Processing. Edited by Pluim, Josien P. W.; Reinhardt, Joseph M.. Proceedings of the SPIE; vol. 6512; (Mar. 2007).
The extended European Search Report, including European Search Opinion of a corresponding European patent application No. 15852840.6, dated Jun. 4, 2018.
The Russian Examination Report of a corresponding Russian patent application No. 2017117301/14(029952), dated Jun. 13, 2018.
The Korean Grant of Patent of corresponding Korean patent application No. 10-2017-7006749, dated Sep. 28, 2018.

* cited by examiner

METHOD AND DEVICE FOR SELECTING DETECTION AREA, AND ELASTICITY DETECTION SYSTEM

CROSS-REFERENCE TO RELATED APPLICATIONS

This application is a continuation of International Application No. PCT/CN2015/081817, filed on Jun. 18, 2015, which claims priority to Chinese Patent Application No. 201410561699.9, filed on Oct. 21, 2014. The contents of the aforementioned applications are hereby incorporated by reference in their entireties.

TECHNICAL FIELD

Embodiments of the present invention relate to the field of medical image processing technology, in particular to a method and a device for selecting a detection area, and an elasticity detection system.

BACKGROUND

Traditional medical imaging, including ultrasound imaging, magnetic resonance imaging (MRI), computed tomography (CT), etc., is applied in many clinical applications for positioning a detection area of an organ tissue, such as elasticity detection and color Doppler ultrasound examination, etc.

At present, an organ tissue detection area is mainly selected in the following two ways: first, the organ tissue in a fixed depth range is seemed as the detection area; second, the organ tissue detection area is artificially selected.

In the first method, while the depth of detection is fixed, however, for different persons, or different positions in one person, the position and shape of the tissue may be different. For example, with respect to the device in the current market for detecting the instantaneous elasticity, the detection range thereof is fixed, that is, the organ tissue of 2.5-6.5 cm subcutaneous, for ordinary people, while for obese or large individuals, 3.5 cm subcutaneous may still be cortical. Therefore, the method of fixed detection range will bring errors for some individuals.

The second method, which employs manual selecting of the detection area, requires the operator to be very familiar with the structure and the image information of the organ tissue, such that the boundary of the organ tissue can be accurately selected, while resulting in a high requirement of the operator; meanwhile, since an artificial selection process is introduced into the detection process, the detection time becomes longer.

In summary, a method for automatically adjusting the detection area is needed.

SUMMARY

The aim of the present invention is to propose a method and a device for selecting a detection area, and an elasticity detection system, thereby automatically adjusting an detection area.

In one aspect, the present invention provides a method for selecting a detection area, including:

determining an organ tissue boundary according to organ tissue information to be recognized, and determining an area surrounded by the organ tissue boundary as an organ tissue area;

dividing the organ tissue information to be recognized into a plurality of detection sub-areas, and calculating feature values of the organ tissue information in the detection sub-areas;

determining an organ tissue boundary area according to the organ tissue information to be recognized;

determining an organ tissue detection area, according to the organ tissue boundary area and the preset feature value condition.

In another aspect, the present invention provides a device for selecting a detection area, including: an area dividing unit, configured to divide organ tissue information to be recognized into a plurality of detection sub-areas; a feature value calculating unit, configured to calculate feature values of the organ tissue information in the detection sub-areas; a boundary area recognizing unit, configured to determine an organ tissue boundary area according to the organ tissue information to be recognized; and a detection area determining unit, configured to determine an organ tissue detection area according to the organ tissue boundary area and a preset feature value condition.

In yet another aspect, the present invention provides an elasticity detection system, including: an information acquiring device, an elasticity imaging device, a probe setting device, a processing device, and a display device, and further including a device for selecting a detection area, provided in any embodiment of the present invention. Where, the information acquiring device is configured to acquire organ tissue information to be recognized; the probe setting device is configured to adjust a position of a probe in the elasticity imaging device, such that a detection range of the probe includes a detection area determined by the device for selecting the detection area; the elasticity imaging device is configured to acquire elasticity information of the organ tissue; and the display device is configure to display the elasticity information in the detection area.

The method and the device for selecting the detection area as well as the elasticity detection system provided in the embodiment of the present invention are capable of automatically adjusting an organ tissue detection area. The method for selecting the detection area provided in the embodiment of the present invention determines the organ tissue boundary area according to the organ tissue information to be recognized, and determines the organ tissue detection area according to the organ tissue boundary area and the preset feature value condition. In this method, the positions and sizes of the detection areas are different when the organ tissue information is different, that is, the method can adjust the position and size of the organ detection area.

BRIEF DESCRIPTION OF THE DRAWINGS

The drawings described herein are intended to provide a further understanding of embodiments of the present invention and form a part of the embodiments of the present invention, while are not to be construed as limiting the embodiments of the present invention. In the drawings.

DESCRIPTION OF EMBODIMENTS

Embodiments of the present invention will now be described in greater detail in conjunction with the accompanying drawings and specific embodiments. It should be understood that the specific embodiments described herein are for the purpose of explaining the embodiments of the present invention only and are not intended to limit the embodiments of the present invention. It also should be noted that, for ease of description, only part rather than all of the embodiments of the present invention are shown in the accompanying drawings.

The First Embodiment

Figure 1:
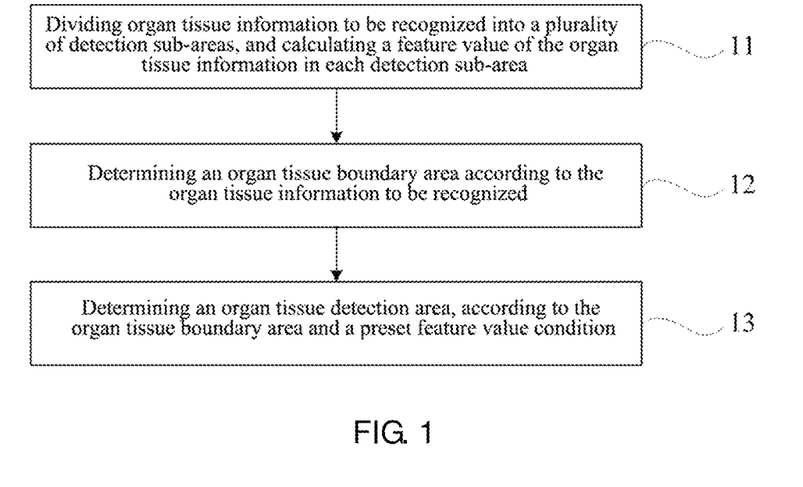
FIG. 1 is an implementation flow chart of a method for selecting a detection area provided in the first embodiment of the present invention.

FIG. 1 is an implementation flow chart of a method for selecting a detection area provided in the first embodiment of the present invention. The method can be performed by a device for selecting the detection area. As shown in FIG. 1, the implementation flow includes:

Step 11: dividing organ tissue information to be recognized into a plurality of detection sub-areas, and calculating a feature value of the organ tissue information in each detection sub-area.

Herein, the organ tissue information to be recognized may include an one-dimensional, two-dimensional, or three-dimensional ultrasound image of the organ tissue, and may also include an one-dimensional, two-dimensional, or three-dimensional ultrasound signal of the organ tissue, such as the organ tissue information may be an A-type ultrasound signal of the organ tissue, an M-type ultrasound signal of the organ tissue, an B-type ultrasound image of the organ tissue, CT image of the organ tissue or MRI image of the organ tissue. Where the feature value of the organ tissue information may be a mean value of the organ tissue information or a standard deviation of the organ tissue information.

Step 12: determining an organ tissue boundary area according to the organ tissue information to be recognized.

The organ tissue boundary area may be determined according to the feature value of the organ tissue information in each detection sub-area calculated in step 11. The organ tissue boundary area of the organ tissue information may also be recognized by using the image processing technique or the signal processing technique with feature of the organ tissue corresponding to the organ tissue information and feature of the organ tissue boundary.

For example, when the organ tissue information is an one-dimensional ultrasonic signal of the organ tissue or a two-dimensional ultrasonic image of the organ tissue, the organ tissue boundary area is determined based on the feature value of the organ tissue information in the detection sub-area; and when the organ tissue information is a three-dimensional ultrasonic signal of the organ tissue, the organ tissue boundary area in the organ tissue information is recognized based on the feature of the organ tissue and the feature of the organ tissue boundary.

Step 13: determining an organ tissue detection area, according to the organ tissue boundary area and a preset feature value condition.

Where the preset feature value condition may be: a distance from the organ tissue boundary area is within a preset depth range. That is, the organ tissue information within the preset depth range from the organ tissue boundary area may be determined as the detection area of the organ tissue information. Where the preset depth range may be from 2.6 cm to 6.5 cm.

Hereinto, if the organ tissue information is an one-dimensional, two-dimensional, or three-dimensional image or signal of an organ tissue, the preset feature value condition may be: the mean value and the standard deviation which are corresponding to the intensity value of the image or signal within each detection sub-area satisfy the preset range.

For example, if the organ tissue information is an one-dimensional ultrasonic signal of the organ tissue, the organ tissue detection area may be determined based on the organ tissue boundary area and the preset feature value condition, which may include: if the standard deviation, corresponding to the intensity value of the ultrasonic signal in each of a plurality of continuous detection sub-areas within the organ tissue boundary area, is less than a standard deviation threshold, the plurality of continuous detection sub-areas are determined as the organ tissue detection area.

For example, if the organ tissue information is a two-dimensional ultrasonic image of the organ tissue or a three-dimensional image of the organ tissue, the organ tissue detection area may be determined based on the organ tissue boundary area and the preset feature value condition, which may include: if the mean value, corresponding to the intensity value of the image in each of a plurality of continuous detection sub-areas within the organ tissue boundary area, is less than a mean value threshold, and if the standard deviation, corresponding to the intensity value of the image in each of a plurality of continuous detection sub-areas within the organ tissue boundary area, is less than a standard deviation threshold, then the plurality of continuous detection sub-areas are determined as the organ tissue detection area.

It should be noted that, the mean value threshold may be 20% of the maximum intensity value of the ultrasonic signal or image in each detection sub-area, and the standard deviation threshold may be 5% of the maximum intensity value of the ultrasonic signal or image in each detection sub-area. For example, the intensity range of the CT image in the detection sub-area of liver tissue can be from 0 HU to 300 HU (Hounsfield unit), the mean threshold thereof can be 60 HU, and the standard deviation threshold thereof can be 15 HU.

Where after the determining the organ tissue detection area based on the organ tissue boundary area and the preset feature value condition, the method may further include: calculating an elasticity value of an organ tissue in the organ tissue detection area. That is, calculating the elasticity value of the organ tissue in the determined organ tissue detection area, so as to realize the ultrasonic detection of the organ tissue.

The method for selecting a detection area provided in the first embodiment of the present invention divides the organ tissue information into a plurality of detection sub-areas and calculates the feature values of the organ tissue information in each detection sub-area, determines the organ tissue boundary area according to the organ tissue information and determines the organ tissue detection area according to the organ tissue boundary area and the preset feature value condition, that is, the method is capable of automatically selecting the detection area. Since in the method for selecting a detection area provided in the first embodiment of the present invention, when the organ tissue information is different, the detection area is different. Namely, in the first embodiment of the present invention, the positions and sizes of the detection area can be automatically adjusted according to the features of organ tissue information in different individuals.

The Second Embodiment

Figure 2:
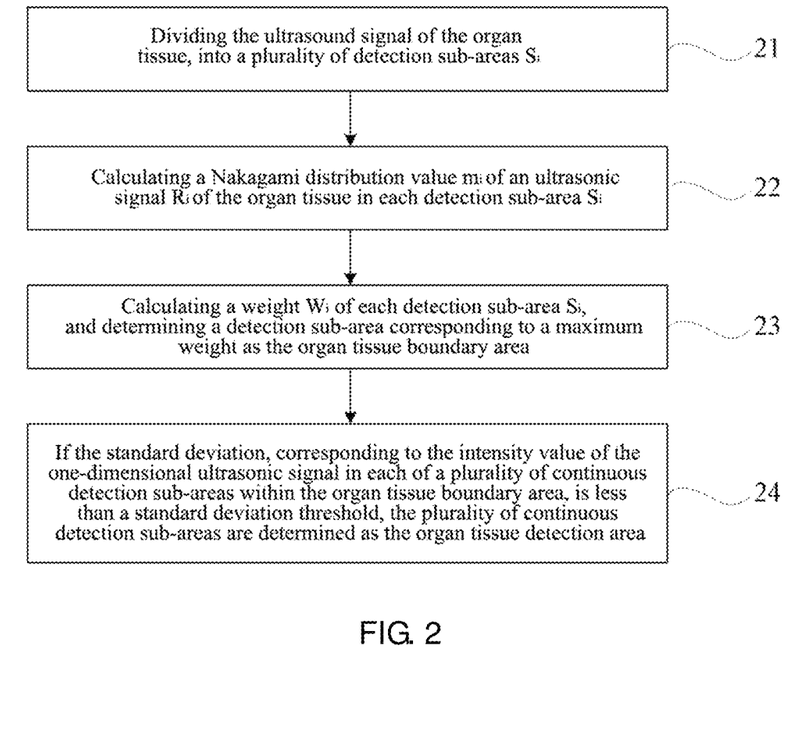
FIG. 2 is an implementation flow chart of a method for selecting a detection area provided in a second embodiment of the present invention.
Figure 3:
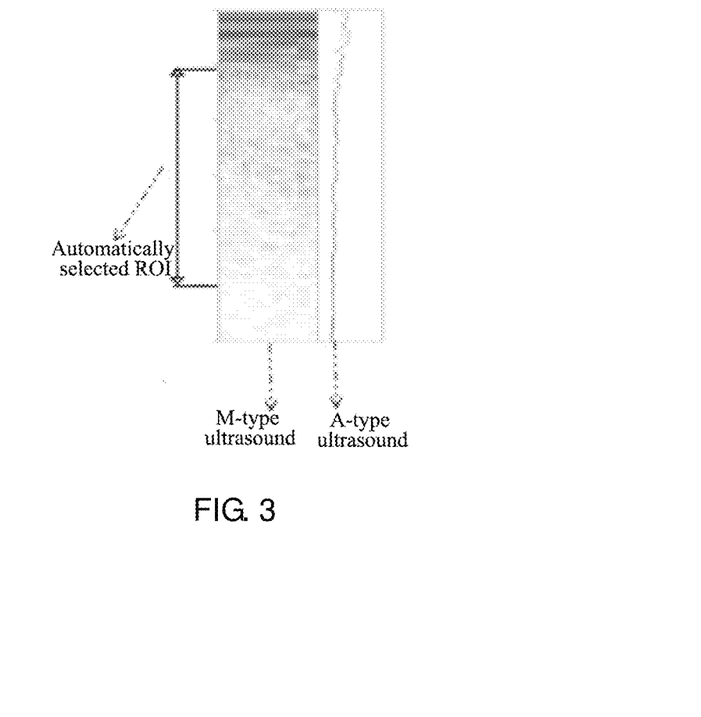
FIG. 3 is an effect view of a selection of a detection area based on an M-type ultrasonic signal of an organ tissue in the second embodiment of the present invention.
Figure 4:
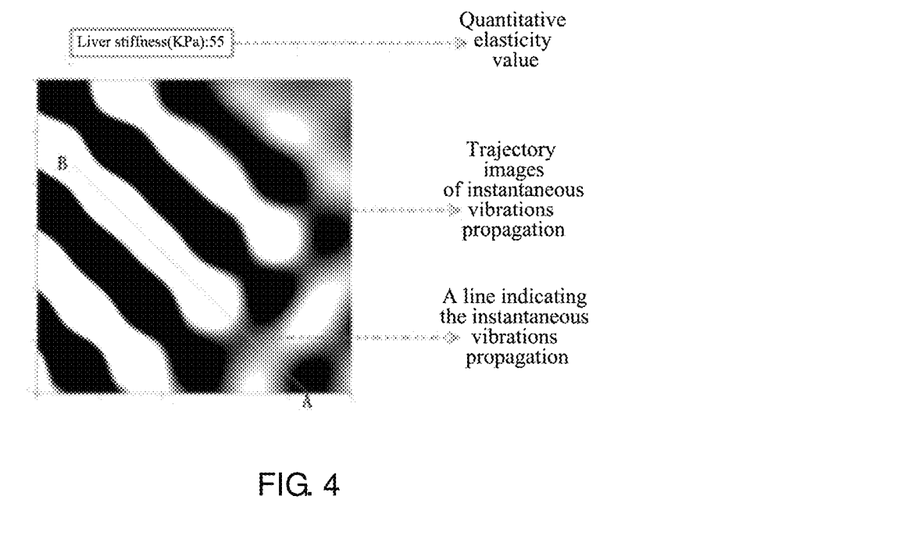
FIG. 4 is a schematic view of the quantitative elasticity modulus of an organ tissue in the second embodiment of the present invention.

FIG. 2 is an implementation flow chart of a method for selecting a detection area provided in a second embodiment of the present invention, which is applicable to an one-dimensional ultrasonic signal of an organ tissue. FIG. 3 is an effect view of a selection of a detection area based on an M-type ultrasonic signal of an organ tissue in the second embodiment of the present invention; FIG. 4 is a schematic view of the quantitative elasticity modulus of an organ tissue in the second embodiment of the present invention. In conjunction with FIG. 2 to FIG. 4, the method further including:

Step 21: dividing the ultrasound signal of the organ tissue, into a plurality of detection sub-areas $S_i$.

The one-dimensional ultrasound signal of the organ tissue may be an A-type ultrasound signal of the organ tissue or an M-type ultrasonic signal of the organ tissue. Assuming that one ultrasonic signal contains n sampling points, and the ultrasonic signal of the corresponding organ tissue has a scanning depth d (unit: mm), and then n/d points are included in per 1 mm depth. The n sampling points are divided into several segments of detection sub-areas $S_i$, and the scanning depth corresponding to the detection sub-areas $S_i$ is $d_i$, where i is an integer, and the scanning depth $d_i$ may be a mean value or an end value of the depths of detection sub-areas $S_i$, herein the scanning depth $d_i$ is the end value.

For example, the n sample points are divided into several segments of detection sub-areas $S_i$ at intervals of z, since the utmost bottom of the image (i.e., corresponding to the deepest portion of the scanning depth) in the ultrasound imaging usually does not contain the detection target, thus the information in the utmost bottom of the image can be ignored, herein, i=1, 2, . . . , [d/z]−1, z is the interval length (unit: mm) of the detection sub-area, and [ ] is the up-rounding operation. In this case, [zn/d] sampling points are included in each segment of detection sub-area. For example, when the scanning depth d of the ultrasonic signal is 20 mm and the interval length z is 3 mm, the n sampling points are divided into [d/z]−1=6 segments of detection sub-area, namely, $S_1$ to $S_6$, where $S_2$ corresponds to the interval of 0~3 mm, $S_2$ corresponds to the interval of 3~6 mm, S6 corresponds to the interval of 15~18 mm, and the utmost bottom of the image (i.e., corresponding to the interval of 18~20 mm) is usually ignored due to not containing the detection target.

Step 22: calculating a Nakagami distribution value $m_i$ of an ultrasonic signal $R_i$ of the organ tissue in each detection sub-area $S_i$.

Herein, the Nakagami statistical model is one of ultrasonic tissue characterization techniques. Specifically, the Nakagami distribution value $m_i$ of the ultrasonic signal $R_i$ corresponding to the image of the organ tissue in each detection sub-area $S_i$ is calculated according to the following formula, $$m_i = \frac{[E(R_i^2)]^2}{E[R_i^2 - E(R_i^2)]^2}$$

Where, the probability density function of the Nakagami distribution is:

$$f(r) = \frac{2m^m r^{2m-1}}{\Gamma(m)\Omega^m} \exp\left(-\frac{m}{\Omega}r^2\right) U(r)$$

Where, E(.) is mean value function, Γ(.) represents Gamma function, $\Omega=E(r^2)$, U(.) represents unit step function, m is the Nakagami distribution value, and r is dependent variable of the probability distribution function f(r), r≥0 and m≥0; for each detection sub-area $S_i$, $m_i$ is m value in the $S_i$ area and $R_i$ is the envelope value of the ultrasonic signal.

An one-dimensional ultrasound signal of the organ tissue follows the pre-Rayleigh distribution when m is in the range of (0, 1); the one-dimensional ultrasound echo signal follows the Rayleigh distribution when m equals to 1; and the one-dimensional ultrasound echo signal follows the post-Rayleigh distribution when m is greater than 1.

Step 23: calculating a weight $W_i$ of each detection sub-area $S_i$ according to the following formula, and determining a detection sub-area corresponding to a maximum weight as the organ tissue boundary area:

$$W_i = \frac{100 * m_i}{\sqrt{d_i}}$$

Where, $d_i$ is the scanning depth corresponding to the detection sub-areas $S_i$, and $d_i$ may be taken as the mean value or end value of depth of the detection sub-areas $S_i$. The weight $W_i$ of each detection sub-area may be traversed, and the detection sub-area corresponding to the maximum weight is taken as the organ tissue boundary area.

Step 24: if the standard deviation, corresponding to the intensity value of the one-dimensional ultrasonic signal in each of a plurality of continuous detection sub-areas within the organ tissue boundary area, is less than a standard deviation threshold, the plurality of continuous detection sub-areas are determined as the organ tissue detection area.

The standard deviation $SD_i$ corresponding to the intensity value of the ultrasonic signal $R_i$ in each detection sub-area $S_i$ within the organ tissue boundary area is calculated, and each detection sub-area within the organ tissue boundary area is traversed, if the standard deviation corresponding to the intensity values of one-dimensional ultrasound signals in each of a plurality of continuous detection sub-areas is less than a standard deviation threshold from a certain detection sub-area, then the plurality of continuous detection sub-areas are determined as the organ tissue detection area, that is, completing the automatic selection of the organ tissue detection area.

As shown in FIG. 4, the quantitative elasticity information may include a numerical value of the quantitative elasticity information of the organ tissue within the detection area determined in Step 23, and the numerical value is measured by the elasticity measurement device, usually in unit of kPa. Where the vertical axis represents the scanning depth and the horizontal axis represents the time. The quantitative elasticity information may also include trajectory image of instantaneous vibrations propagating over time along the depth during the transient elastic imaging process. The image also contains line segment AB indicating the propagation of the instantaneous vibrations. In addition, according to the quantitative elasticity information of the organ tissue shown in FIG. 4, the elasticity modulus of the organ tissue can be calculated by calculating the propagation velocity of the shear wave generated by the instantaneous vibration in the area indicated by the indication mark.

The method for selecting a detection area provided in the second embodiment of the present invention can automatically select an organ tissue detection area through an A-type or an M-type ultrasound signal of the organ tissue. In addition, the algorithm possesses high recognition efficiency for the organ tissue boundary due to its low complexity, thereby realizing a real-time automatic localization of the organ tissue boundary.

The Third Embodiment

Figure 5:
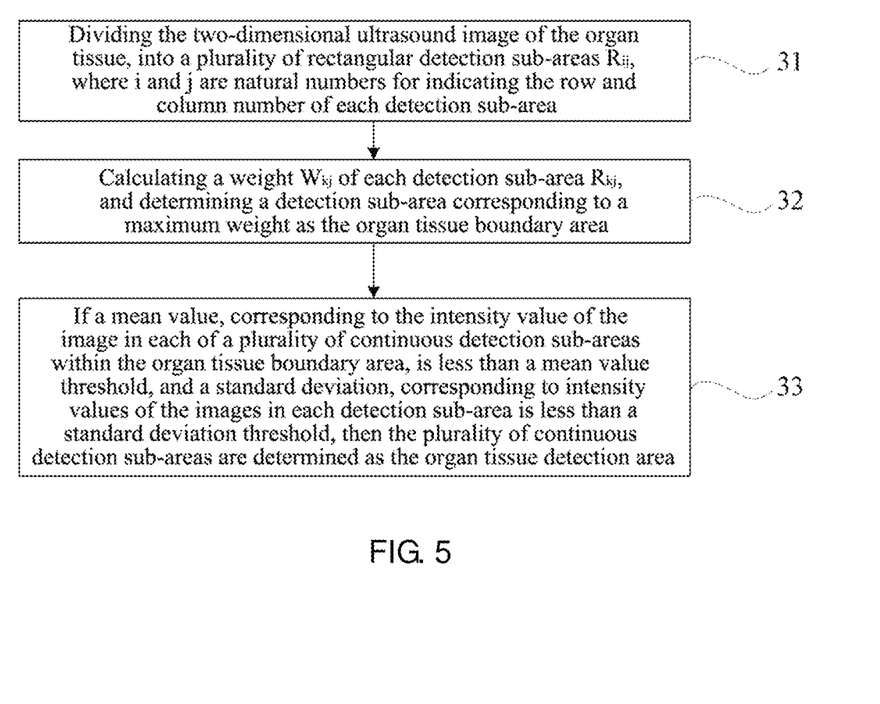
FIG. 5 is an implementation flow chart of a method for selecting a detection area provided in a third embodiment of the present invention.
Figure 6:
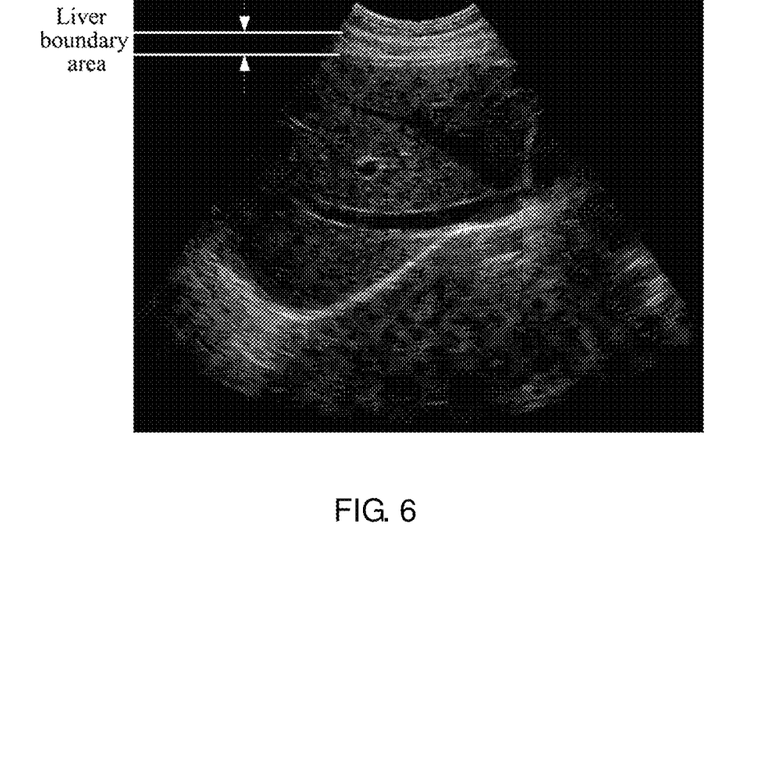
FIG. 6 is an effect view of a selection of a detection area based on a B-type ultrasonic signal of an organ tissue in the third embodiment of the present invention.
Figure 7:
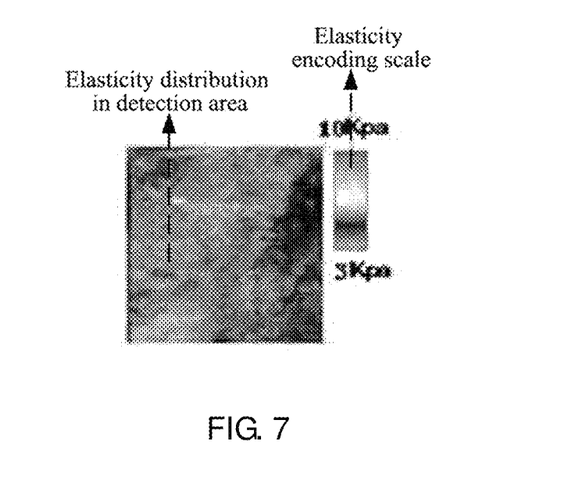
FIG. 7 is a schematic view of a quantitative elasticity modulus of the organ tissue in the third embodiment of the present invention.

FIG. 5 is an implementation flow chart of a method for selecting a detection area provided in a third embodiment of the present invention; FIG. 6 is an effect view of a selection of a detection area based on a B-type ultrasonic signal of an organ tissue in the third embodiment of the present invention; FIG. 7 is a schematic view of a quantitative elasticity modulus of the organ tissue in the third embodiment of the present invention. Referring to FIG. 5 to FIG. 7, the method includes:

Step 31: dividing the two-dimensional ultrasound image of the organ tissue, into a plurality of rectangular detection sub-areas $R_{ij}$, where i and j are natural numbers for indicating the row and column number of each detection sub-area.

The two-dimensional ultrasound image of the organ tissue may be a B-type ultrasound image of an organ tissue. Assuming that the size of the B-type ultrasound image is w*h, where w is a width of the two-dimensional ultrasound image of the organ tissue, h is a height of the two-dimensional ultrasound image of the organ tissue (w and h are both in unit of pixel), and the corresponding scanning depth is d (unit: mm), then h/d pixels are contained in a 1 mm depth on one scan line in the depth direction. The B-type image having a size of w*h is divided into a plurality of rectangular detection sub-areas $R_{ij}$.

For example, a B-type image having a size of w*h is divided into a plurality of square detection sub-areas $R_{ij}$ with a side length of z, which is similarly to the first embodiment.

Since the utmost bottom of the image (i.e., corresponding to the deepest portion of the scanning depth) and the utmost edge in the width direction in the ultrasound imaging usually do not contain the detection target, the information in the utmost bottom of the image and the utmost edge in the width direction can be ignored, herein $$i = 1, 2, \ldots, \left[\frac{d}{z}\right] - 1, j = 1, 2, \ldots, \left[\frac{wd}{hz}\right] - 1,$$

where z is the side length (unit: mm) of the square detection sub-area and [ ] is the up-rounding operation. At this time, both the width and height of each square detection sub-area $R_{ij}$ are [zh/d] pixels.

Step 32: calculating a weight $W_{ij}$ of each detection sub-area $R_{ij}$, and determining a detection sub-area corresponding to a maximum weight as the organ tissue boundary area. Here, in order to reduce the computation burden, only a half of the detection sub-area weights are calculated. For example, the two-dimensional ultrasound image may be divided into two along a centerline, and only the weight $W_{kj}$ ($k=i_{max}/2$) of each detection sub-area $R_{kj}$ in a half of the two-dimensional ultrasound image above the centerline is calculated, so as to find a boundary sub-area above the centerline, and then the boundary sub-area is extended in the width direction (lateral direction) to obtain the whole boundary area. Where, the weight $W_{kj}$ can be calculated according to the following formula:

$$W_{kj} = \frac{M_{kj}}{SD_{kj} * \sqrt{d_{kj}}}$$

Where, $M_{kj}$ is a grayscale mean value of the two-dimensional ultrasound image of the organ tissue in the detection sub-areas $R_{kj}$, $SD_{kj}$ is a grayscale standard deviation of the two-dimensional ultrasound image of the organ tissue in the detection sub-areas $R_{kj}$, and $d_{kj}$ is a scanning depth of the detection sub-areas $R_{kj}$. According to $k=i_{max}/2$, when the two-dimensional ultrasound image of the organ tissue is divided into rectangular areas with side lengths of z, $$k = \frac{1}{2}\left[\left[\frac{wd}{hz}\right] - 1\right],$$

k is an integer, and $i_{max}$ is the maximum value of i.

For example, since the liver capsule area exhibits a homogeneous high echo on a B-type ultrasound image, the grayscale mean value of the organ tissue boundary area is large; in addition, since the liver capsule area possesses uniformity in the B-type ultrasound image, the grayscale standard deviation is small. In order to avoid a black background area on both sides of the fan-shaped B-type ultrasound image when the convex array probe is scanned, a searching is performed from the detection sub-areas locating at the centerline of the B-type ultrasound image. If the detection sub-area $R_{kl}$ is the one having the largest weight in a series of the detection area $R_{kj}$, the detection sub-area $R_{kl}$ is determined as a boundary area of the liver tissue.

Step 33: if a mean value, corresponding to the intensity value of the image in each of a plurality of continuous detection sub-areas within the organ tissue boundary area, is less than a mean value threshold, and a standard deviation, corresponding to intensity values of the images in each detection sub-area is less than a standard deviation threshold, then the plurality of continuous detection sub-areas are determined as the organ tissue detection area.

Starting from a certain detection sub-area, if a mean value of the intensity values of the images in each of a plurality of continuous detection sub-areas is less than a mean value threshold, and a standard deviation of the intensity values of the images is less than a standard deviation threshold, then the plurality of continuous detection sub-areas are determined as a detection area, that is, completing the automatic selection of the detection area.

As shown in FIG. 7, the quantitative elasticity information includes a numerical value (in unit of kPa) of the quantitative elasticity information of the organ tissue in the detection area shown in the structural view of the organ tissue obtained by the elasticity measurement. The elasticity modulus information includes an elasticity modulus distribution of the organ tissue structure in the detection area. Where the elasticity modulus distribution can be color-encoded, with different colors representing different elasticity modulus; the elasticity modulus distribution may also be represented in grayscale or other encoding forms, that is, the color-encoding grayscale-encoding or other encoding forms can be applied to represent intensity values of the two-dimensional ultrasound image of the organ tissue within the detection sub-area. Correspondingly, the elasticity modulus distribution further includes a scalogram representing the elasticity modulus encoding.

The method for selecting a detection area provided in the third embodiment of the present invention can automatically select an organ tissue detection area via a B-type ultrasound image of an organ tissue. In addition, the algorithm possesses high recognition efficiency for the organ tissue boundary due to its low complexity, thereby realizing a real-time automatic localization of the organ tissue boundary.

The Fourth Embodiment

Figure 8:
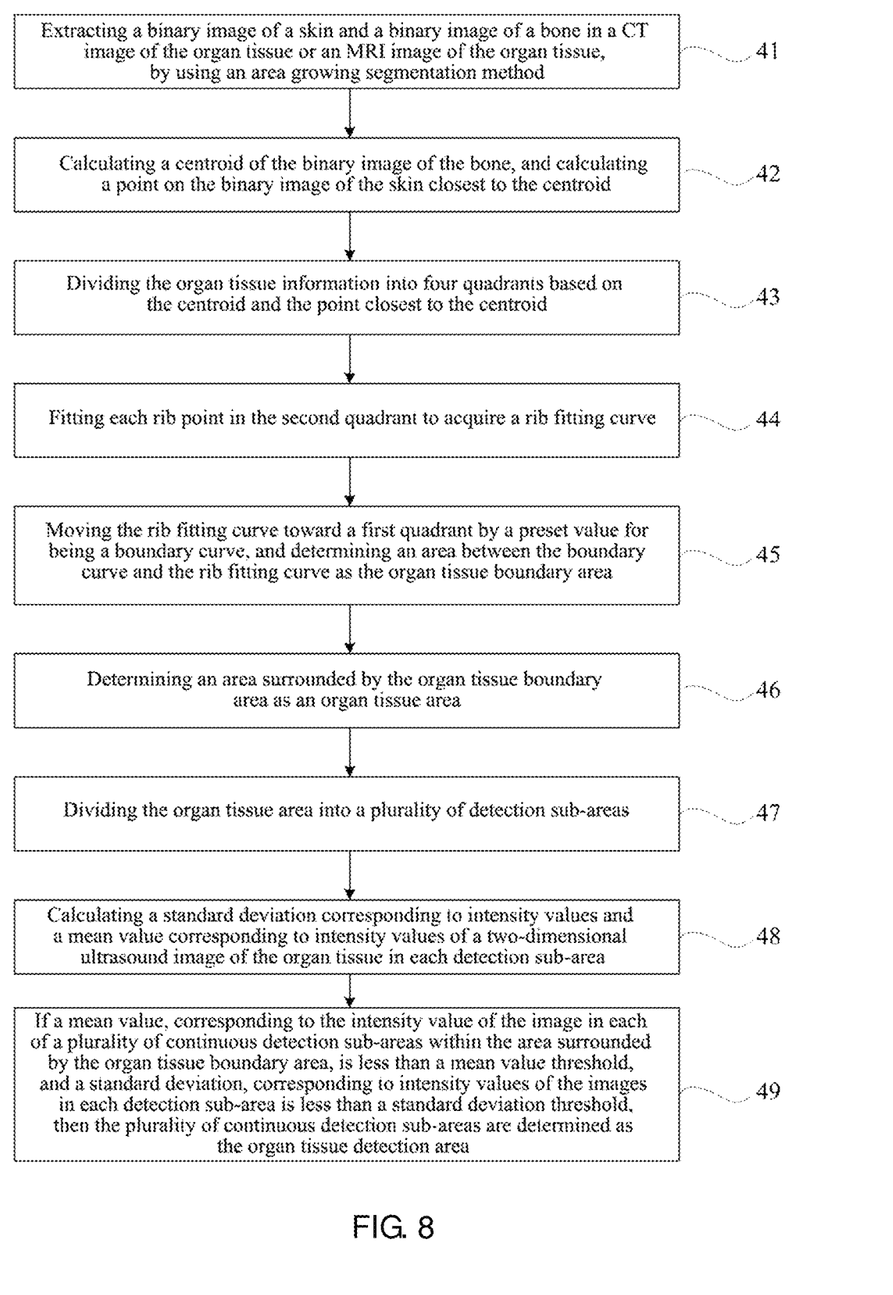
FIG. 8 is an implementation flow chart of a method for selecting a detection area provided in a fourth embodiment of the present invention.
Figure 9:
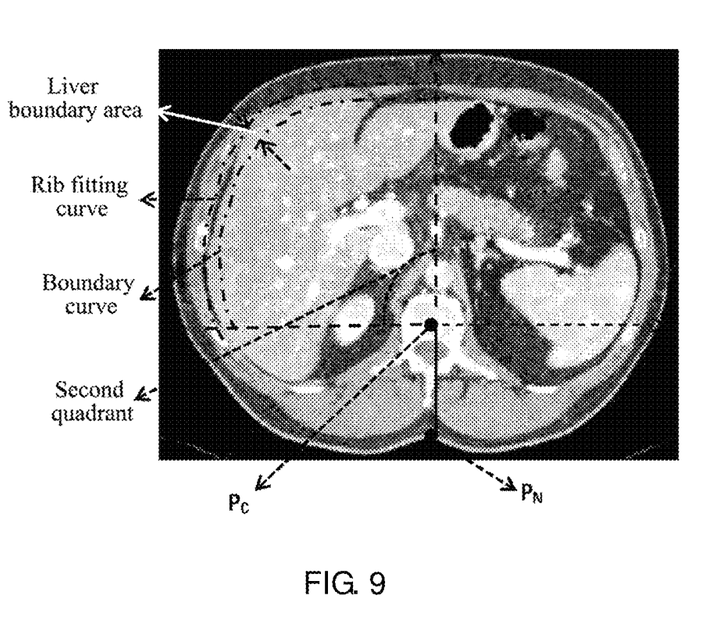
FIG. 9 is an effect view of a three-dimensional image boundary based on an organ tissue in the fourth embodiment of the present invention.
Figure 10:
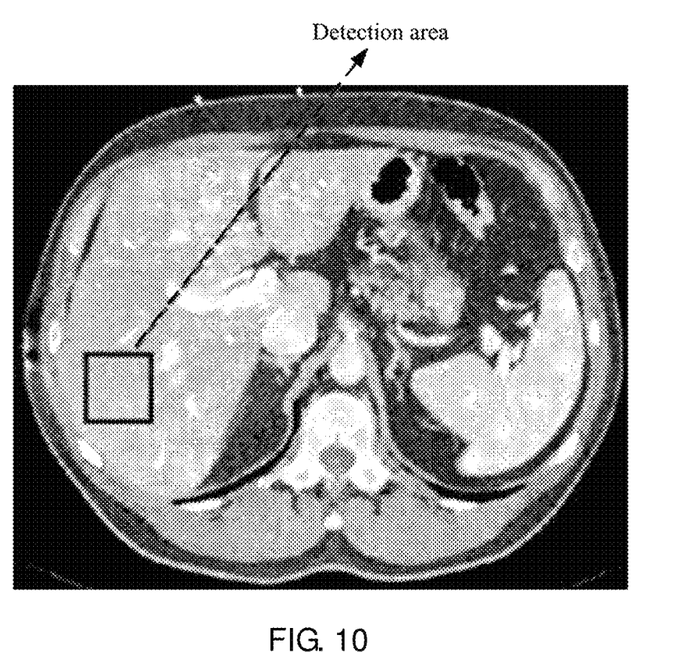
FIG. 10 is an effect view of a selection of a detection area based on a three-dimensional image of an organ tissue in the fourth embodiment of the present invention.
Figure 11:
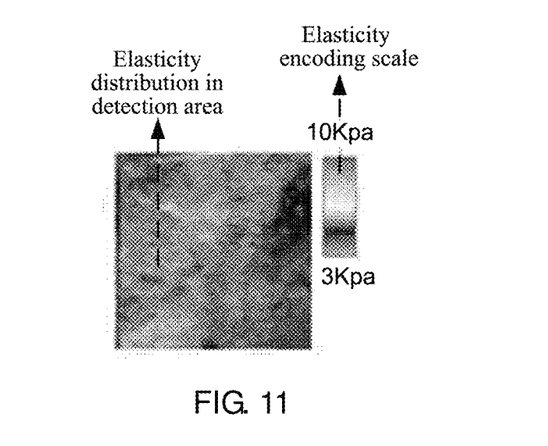
FIG. 11 is a schematic view of a quantitative elasticity modulus of an organ tissue in the fourth embodiment of the present invention.

FIG. 8 is an implementation flow chart of a method for selecting a detection area provided in a fourth embodiment of the present invention; FIG. 9 is an effect view of a three-dimensional image boundary based on an organ tissue in the fourth embodiment of the present invention; FIG. 10 is an effect view of a selection of a detection area based on a three-dimensional image of an organ tissue in the fourth embodiment of the present invention; and FIG. 11 is a schematic view of a quantitative elasticity modulus of an organ tissue in the fourth embodiment of the present invention. Referring to FIG. 8 to FIG. 11, the method includes:

Step 41: extracting a binary image of a skin and a binary image of a bone in a CT image of the organ tissue or an MRI image of the organ tissue, by using an area growing segmentation method.

First, the binary image of the skin is extracted. Pixel with image coordinate of (0, 0) is used as a seed point, and the binary image of the skin is extracted by using the area growing segmentation method, where the area growing criterion of air CT value is [−1024, −500] HU (Hounsfield unit, Heinz).

Next, the binary image of the bone is extracted, including a binary image of the vertebra and a binary image of the rib. Threshold segmentation with a threshold range of [350, 1024] HU is performed on the whole image to extract the binary image of bone.

Step 42: calculating a centroid of the binary image of the bone, and calculating a point on the binary image of the skin closest to the centroid.

The centroid $P_C$ of the binary image of the bone is calculated. Since the ribs are generally symmetrical about the vertebra and the vertebra has a large proportion in the bone image, the centroid of the bone image is the centroid $P_C$ of the vertebra.

A point on the binary image of the skin that is closest to the centroid $P_C$ is denoted as $P_N$, starting with the vertebra centroid $P_C$.

Step 43: dividing the organ tissue information into four quadrants based on the centroid and the point closest to the centroid.

The CT image is divided into four quadrants by using the centroid $P_C$ and the point $P_N$ closest to the centroid, that is, a straight line passing the centroid $P_C$ and the point $P_N$ closest to the centroid $P_C$ is taken as a vertical axis, and a straight line passing the centroid $P_C$ and perpendicular to the vertical axis is taken as the horizontal axis. Taking the liver tissue as an example, most area of the liver is in the second the liver quadrant.

Step 44: fitting each rib point in the second quadrant to acquire a rib fitting curve.

Each rib point in the second quadrant is fitted with a B-spline curve or a skin curve to obtain a rib fitting curve.

Step 45: moving the rib fitting curve toward a first quadrant by a preset value for being a boundary curve, and determining an area between the boundary curve and the rib fitting curve as the organ tissue boundary area.

Since the rib curve is close to the liver capsule, the rib curve is moved inwardly by a preset value and taken as a boundary curve, and the area between the boundary curve and the rib fitting curve is determined as the organ tissue boundary area.

Herein, the preset value may be 5 mm.

Step 46: determining an area surrounded by the organ tissue boundary area as an organ tissue area.

Step 47: dividing the organ tissue area into a plurality of detection sub-areas.

Step 48: calculating a standard deviation corresponding to intensity values and a mean value corresponding to intensity values of a two-dimensional ultrasound image of the organ tissue in each detection sub-area.

Step 49: if a mean value, corresponding to the intensity value of the image in each of a plurality of continuous detection sub-areas within the area surrounded by the organ tissue boundary area, is less than a mean value threshold, and a standard deviation, corresponding to intensity values of the images in each detection sub-area is less than a standard deviation threshold, then the plurality of continuous detection sub-areas are determined as the organ tissue detection area.

Each detection sub-area within the liver is searched starting from the boundary of the liver tissue, and if a mean value of the intensity values of the images in each of a plurality of continuous detection sub-areas is less than a mean value threshold, and a standard deviation of the intensity values of the images is less than a standard deviation threshold, then the plurality of continuous detection sub-areas are determined as a detection area, that is, completing the automatic selection of the detection area.

As shown in FIG. 11, the quantitative elasticity information includes a numerical value (in unit of kPa) of the quantitative elasticity information of the organ tissue shown in the structural view of the organ tissue obtained by the elasticity measurement. Where, the elasticity modulus information also includes an elasticity modulus distribution of the tissue in the area indicated by an indicator mark in a tissue structural view. Where the distribution image can be color-encoded, with different colors representing different elasticity modulus; the distribution image may also be represented in grayscale or other encoding forms. Correspondingly, the elasticity modulus distribution further includes a scalogram representing the elasticity modulus encoding.

It is to be noted that, when the automatic recognition of the organ tissue boundary area and the automatic adjustment of the position and size of the detection area are realized by using a CT image or a MRI image, the automatically selected detection area can be 3D geometry.

Taken CT sequential images as an example, for each frame of the CT images, the detection area of the image in the frame of the organ tissue image is automatically selected by using the method for selecting the detection area provided in the present embodiment. And then a three-dimensional geometry, i.e., three-dimensional detection area, is reconstructed by using each detection area corresponding to each frame of images. The elasticity detection probe is used to detect the elasticity information in the two-dimensional detection area of each frame of CT images and reconstruct the three-dimensional elasticity distribution of the organ tissue, thereby obtaining the three-dimensional elasticity information of the organ tissue.

The method for selecting a detection area provided in the fourth embodiment of the present invention can automatically select an organ tissue detection area by a three-dimensional image of an organ tissue, for example, the CT image of the organ tissue or the MRI image of the organ tissue. In addition, the algorithm possesses high recognition efficiency for the organ tissue boundary due to its low complexity, thereby realizing a real-time automatic localization of the organ tissue boundary.

The Fifth Embodiment

Figure 12:
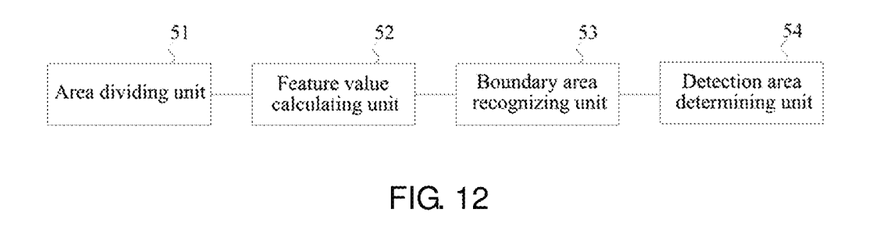
FIG. 12 is a schematic structural view of a device for selecting a detection area provided in a fifth embodiment of the present invention.

FIG. 12 is a schematic structural view of a device for selecting a detection area provided in a fifth embodiment of the present invention. As shown in FIG. 12, the device for selecting the detection area described in the present embodiment may include: an area dividing unit 51, configured to divide the organ tissue information to be recognized into a plurality of detection sub-areas; a feature value calculating unit 52, configured to calculate a feature value of the organ tissue information in the detection sub-area; a boundary area recognizing unit 53, configured to determine an organ tissue boundary area according to the organ tissue information to be recognized; and a detection area determining unit 54, configured to determine an organ tissue detection area according to the organ tissue boundary area and a preset feature value condition.

Where, the device may further include: an elasticity value calculating unit, configured to calculate an elasticity value of an organ tissue in the organ tissue detection area.

Where the preset feature value condition may be such that a distance from the organ tissue boundary area is within a preset depth range.

Where, if the organ tissue information is an one-dimensional, two-dimensional or three-dimensional image or signal of the organ tissue, the preset feature value condition may be such that both a mean value and a standard deviation corresponding to intensity values of the image or signal in each detection sub-area satisfy a preset range.

Where, if the organ tissue information is an one-dimensional ultrasound signal of an organ tissue, the boundary area recognizing unit 53 may include: a calculating sub-unit, configured to calculate a Nakagami distribution value $m_i$ of an one-dimensional ultrasound signal $R_i$ of the organ tissue in each detection sub-area $S_i$; and an area recognizing sub-unit, configured to calculate a weight $W_i$ of each detection sub-area $S_i$ according to the following formula and determine a detection sub-area corresponding to a maximum weight as the organ tissue boundary area:

$$W_i = \frac{100 * m_i}{\sqrt{d_i}}$$

Where, $d_i$ is a scanning depth corresponding to the detection sub-area $S_i$.

Where, if the organ tissue information is a two-dimensional ultrasound image of the organ tissue, the area dividing unit 51 may be specifically configured to calculate the weight $W_{kj}$ of each detection sub-area $R_{kj}$ according to the following formula and determine a detection sub-area corresponding to a maximum weight as the organ tissue boundary area:

$$W_{kj} = \frac{M_{kj}}{SD_{kj} * \sqrt{d_{kj}}}$$

Where, $M_{kj}$ is a grayscale mean value of the two-dimensional ultrasound image of the organ tissue in the detection sub-area $R_{kj}$; $SD_{kj}$ is a grayscale standard deviation of the two-dimensional ultrasound image of the organ tissue in the detection sub-area $R_{kj}$; $d_{kj}$ is a scanning depth corresponding to the detection sub-area $R_{kj}$; and $k=i_{max}/2$.

The two-dimensional ultrasound image of the organ tissue is divided into a plurality of rectangular detection sub-areas $R_{ij}$; the boundary area recognizing unit 53 can be specifically configured to calculate a weight $W_{kj}$ of each detection sub-area $R_{kj}$ according to the following formula, and determine a detection sub-area corresponding to a maximum weight as the organ tissue boundary area:

$$W_{kj} = \frac{M_{kj}}{SD_{kj} * \sqrt{d_{kj}}}$$

Where, $M_{kj}$ is a grayscale mean value of the two-dimensional ultrasound image of an organ tissue in the detection sub-area $R_{kj}$; $SD_{kj}$ is a grayscale standard deviation of the two-dimensional ultrasound image of the organ tissue in the detection sub-area; $d_{kj}$ is a scanning depth corresponding to the detection sub-area, and $k=i_{max}/2$.

Where if the organ tissue information is a CT image of the organ tissue or an MRI image of the organ tissue, the boundary area recognizing unit 53 may specifically include: a binary image acquiring sub-unit, configured to extract a binary image of a skin and a binary image of a bone in the CT image of the organ tissue or the MRI image of the organ tissue by using an image segmentation method; and a feature point determining sub-unit, configured to calculate a centroid of the binary image of the bone, and calculate a point on the binary image of the skin closest to the centroid; an image dividing sub-unit, configured to divide the image of the organ tissue into four quadrants according to the centroid and the point closest to the centroid; a curve fitting sub-unit, configured to fit each rib point in the second quadrant to acquire a rib fitting curve; and a boundary area determining sub-unit, configured to move the rib fitting curve toward a first quadrant by a preset value for being a boundary area curve, and determine an area between the boundary area curve and the rib fitting curve as the organ tissue boundary area.

A device for selecting a detection area provided in the fifth embodiment of the present invention divides the organ tissue information to be recognized into a plurality of detection sub-areas, calculates a feature value of the organ tissue information in the detection sub-areas, determines an organ tissue boundary area according to the organ tissue information to be recognized, and determines an organ tissue detection area according to the determined organ tissue boundary area and a preset feature value condition. In this device, the position and size of the detection area are different when the organ tissue information is different, i.e., the device can adjust the position and size of the detection area.

The Sixth Embodiment

Figure 13:
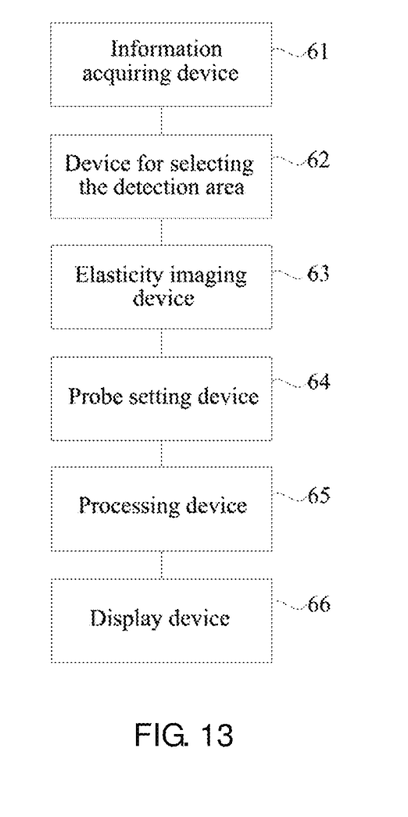
FIG. 13 is a schematic structural view of an elasticity detection system provided in a sixth embodiment of the present invention.

FIG. 13 is a schematic structural view of an elasticity detection system provided in a sixth embodiment of the present invention. As shown in FIG. 13, the elasticity detection system described by the present embodiment may include an information acquiring device 61, an elasticity imaging device 63, a probe setting device 64, a processing device 65, and a display device 66, further includes a device for selecting the detection area 62 provided in the fifth embodiment of the present invention, where the information acquiring device 61 is configured to acquire organ tissue information to be recognized; the probe setting device 64 is configured to adjust a position of a probe in the elasticity imaging device such that the detection range of the probe includes a detection area determined by the device for selecting the detection area; the elasticity imaging device 63 is configured to acquire elasticity information of an organ tissue; the processing device 65 is configured to process the elasticity information acquired by the elasticity imaging device, thereby acquiring the elasticity information in the detection area; and the display device 66 is configured to display the elasticity information in the detection area.

The elasticity detection system provided in the sixth embodiment of the present invention is capable of automatically recognizing the organ tissue boundary area and automatically adjusting the position and size of the detection area, thereby saving the elastic detection time, reducing the operation difference among different operators and the same operator with different operations, and realizing a accurate, fast, highly reproducible elasticity detection of the organ tissue.

The foregoing descriptions are merely preferred embodiments of the present invention, and are not intended to limit the embodiments of the present invention. Various modifications and changes can be performed on the embodiments of the present invention by those skilled in the art. Any modifications, equivalent substitutions, improvements and the like within the spirit and principle of the embodiments of the present invention shall be encompassed within the protection scope of the embodiments of the present invention.

What is claimed is:

1. A method for selecting an organ tissue detection area, comprising executing, by a processor, the following steps: dividing organ tissue information to be recognized into a plurality of detection sub-areas, and calculating a feature value of the organ tissue information in each detection sub-area;
determining an organ tissue boundary area according to the feature value of the organ tissue information to be recognized; and
determining an organ tissue detection area according to the organ tissue boundary area and a preset feature value condition,
the organ tissue information is a one-dimensional, two-dimensional or three-dimensional image or signal of an organ tissue, the preset feature value condition is: a standard deviation corresponding to an intensity value of the image or signal in each detection sub-area satisfy a preset range, and the determining the organ tissue detection area according to the organ tissue boundary area and the preset feature value condition comprises:
when the standard deviation corresponding to the intensity value of the image or signal in each of a plurality of continuous detection sub-areas within the organ tissue boundary area, is less than a standard deviation threshold, the plurality of continuous detection sub-areas are determined as the organ tissue detection area.

2. The method according to claim 1, after the determining the organ tissue detection area according to the organ tissue boundary area and the preset feature value condition, further comprising executing, by the processor, the following step:
calculating an elasticity value of an organ tissue in the organ tissue detection area.

3. The method according to claim 1, wherein the organ tissue information is a one-dimensional ultrasonic signal of the organ tissue,
the determining an organ tissue boundary area according to the feature value of the organ tissue information to be recognized, comprises:
calculating a Nakagami distribution value $m_i$ of a one-dimensional ultrasonic signal $R_i$ of the organ tissue in each detection sub-area $S_i$;
calculating a weight $W_i$ of each detection sub-area $S_i$ according to the following formula, and determining a detection sub-area corresponding to a maximum weight as the organ tissue boundary area:

$$W_i = \frac{100 * m_i}{\sqrt{d_i}}$$

where $d_i$ is a scanning depth corresponding to the detection sub-areas $S_i$, and i is a natural number.

4. The method according to claim 1, wherein if the organ tissue information is a two-dimensional ultrasound image of the organ tissue,
the dividing organ tissue information to be recognized into a plurality of detection sub-areas comprises: dividing the two-dimensional ultrasonic image of the organ tissue into a plurality of rectangular detection sub-areas $R_{ij}$, wherein i and j are natural numbers;
the determining an organ tissue boundary area according to the organ tissue information to be recognized comprises:
calculating a weight $W_{ij}$ of each detection sub-area $R_{ij}$ according to the following formula, and determining a detection sub-area corresponding to a maximum weight as the organ tissue boundary area:

$$W_{kj} = \frac{M_{kj}}{SD_{kj} * \sqrt{d_{kj}}}$$

where $M_{kj}$ is a grayscale mean value of the two-dimensional ultrasound image of the organ tissue in the detection sub-areas $R_{kj}$, $SD_{kj}$ is a grayscale standard deviation of the two-dimensional ultrasound image of the organ tissue in the detection sub-areas $R_{kj}$, $d_{kj}$ is a scanning depth corresponding to the detection sub-areas $R_{kj}$, $k=i_{max}/2$, k is natural number, and $i_{max}$ is the maximum value of i.

5. The method according to claim 1, wherein if the organ tissue information is a CT image of the organ tissue or an MRI image of the organ tissue, the determining an organ tissue boundary area according to the organ tissue information to be recognized comprises:

extracting a binary image of a skin and a binary image of a bone in the CT image of the organ tissue or the MRI image of the organ tissue by using an image segmentation method;

calculating a centroid of the binary image of the bone, and calculating a point on the binary image of the skin closest to the centroid;

dividing the CT image of the organ tissue or the MRI image of the organ tissue into four quadrants according to the centroid and the point closest to the centroid;

fitting each rib point in the second quadrant to acquire a rib fitting curve;

moving the rib fitting curve toward a first quadrant by a preset value for being a boundary area curve, and determining an area between the boundary area curve and the rib fitting curve as the organ tissue boundary area.

6. A device for selecting an organ tissue detection area, comprising a processor, wherein the processor is configured to:

divide organ tissue information to be recognized into a plurality of detection sub-areas;

calculate a feature value of the organ tissue information in each detection sub-area;

determine an organ tissue boundary area according to the feature value of the organ tissue information to be recognized; and determine an organ tissue detection area according to the organ tissue boundary area and a preset feature value condition, the organ tissue information is a one-dimensional, two-dimensional or three-dimensional image or signal of an organ tissue, the preset feature value condition is: a standard deviation corresponding to an intensity value of the image or signal in each detection sub-area satisfy a preset range, and the determining the organ tissue detection area according to the organ tissue boundary area and the preset feature value condition comprises:

when the standard deviation corresponding to the intensity value of the image or signal in each of a plurality of continuous detection sub-areas within the organ tissue boundary area, is less than a standard deviation threshold, the plurality of continuous detection sub-areas are determined as the organ tissue detection area.

7. The device according to claim 6, wherein the processor is further configured to:

calculate an elasticity value of an organ tissue in the organ tissue detection area.

8. The device according to claim 6, wherein the organ tissue information is a one-dimensional ultrasonic signal of the organ tissue, the processor is further configured to:

calculate a Nakagami distribution value $m_i$ of a one-dimensional ultrasonic signal $R_i$ of the organ tissue in each detection sub-area $S_i$;

calculate a weight $W_i$ of each detection sub-area $S_i$ according to the following formula, and determine a detection sub-area corresponding to a maximum weight as the organ tissue boundary area:

$$W_i = \frac{100 * m_i}{\sqrt{d_i}}$$

wherein $d_i$ is a scanning depth corresponding to the detection sub-area $S_i$, and i is a natural number.

9. The device according to claim 6, wherein if the organ tissue information is a two-dimensional ultrasound image of the organ tissue, the area dividing unit is specifically configured to divide the two-dimensional ultrasonic image of the organ tissue into a plurality of rectangular detection sub-areas $R_{ij}$, wherein i and j are natural numbers;

the boundary area recognizing unit is specifically configured to:

calculate, a weight $W_{kj}$ of each detection sub-area $R_{kj}$ according to the following formula, and determine, a detection sub-area corresponding to a maximum weight as the organ tissue boundary area:

$$W_{kj} = \frac{M_{kj}}{SD_{kj} * \sqrt{d_{kj}}}$$

wherein, $M_{kj}$ is a grayscale mean value of the two-dimensional ultrasonic image of the organ tissue in the detection sub-area $R_{kj}$, $SD_{kj}$ is a grayscale standard deviation of the two-dimensional ultrasonic image of the organ tissue in the detection sub-area $R_{kj}$, $d_{kj}$ is a scanning depth corresponding to the detection sub-area $R_{kj}$, $k=i_{max}/2$, k is a natural number, and $i_{max}$ is a maximum value of i.

10. The device according to claim 6, wherein if the organ tissue information is a CT image of the organ tissue or an MRI image of the organ tissue, the boundary area recognizing unit specifically comprises:

a binary image acquiring sub-unit, configured to extract a binary image of a skin and a binary image of a bone in the CT image of the organ tissue or the MRI image of the organ tissue by using an image segmentation method;

a feature point determining sub-unit, configured to calculate a centroid of the binary image of the bone, and calculate a point on the binary image of the skin closest to the centroid;

an image dividing sub-unit, configured to divide the CT image of the organ tissue and the MRI image of the organ tissue into four quadrants according to the centroid and the point closest to the centroid;

a curve fitting sub-unit, configured to fit each rib point in the second quadrant to acquire a rib fitting curve; and a boundary area determining sub-unit, configured to move the rib fitting curve toward a first quadrant by a preset value for being a boundary area curve, and determine an area between the boundary area curve and the rib fitting curve as the organ tissue boundary area.

11. An elasticity detection system, comprising a device for selecting an organ tissue detection area according to claim 6, wherein the processor is configured to:

acquire organ tissue information to be recognized;

adjust a position of a probe in the elasticity imaging device, such that a detection range of the probe comprises an organ tissue detection area determined by the device for selecting the organ tissue detection area;

acquire elasticity information of an organ tissue; and display the elasticity information in the organ tissue detection area.

12. An elasticity detection system, comprising a device for selecting an organ tissue detection area according to claim 7, wherein the processor is configured to:

acquire organ tissue information to be recognized;

adjust a position of a probe in the elasticity imaging device, such that a detection range of the probe comprises an organ tissue detection area determined by the device for selecting the organ tissue detection area;

acquire elasticity information of an organ tissue; and display the elasticity information in the organ tissue detection area.

13. An elasticity detection system, comprising a device for selecting an organ tissue detection area according to claim 8, wherein the processor is configured to:

acquire organ tissue information to be recognized;

adjust a position of a probe in the elasticity imaging device, such that a detection range of the probe comprises a detection area determined by the device for selecting the detection area;

acquire elasticity information of an organ tissue; and display the elasticity information in the detection area.

14. An elasticity detection system, comprising: an information acquiring device, an elasticity imaging device, a probe setting device, and a display device, and further comprising a device for selecting a detection area according to claim 9, wherein, the information acquiring device, is configured to acquire organ tissue information to be recognized;

the probe setting device, is configured to adjust a position of a probe in the elasticity imaging device, such that a detection range of the probe comprises a detection area determined by the device for selecting the detection area;

the elasticity imaging device, is configured to acquire elasticity information of an organ tissue; and the display device, is configured to display the elasticity information in the detection area.

* * * * *